US012426861B2

United States Patent
Stand, III

(10) Patent No.: US 12,426,861 B2
(45) Date of Patent: Sep. 30, 2025

(54) BIOPSY DEVICE

(71) Applicant: HOLOGIC, INC., Marlborough, MA (US)

(72) Inventor: Joseph A. Stand, III, Holden, MA (US)

(73) Assignee: HOLOGIC, INC., Marlborough, MA (US)

( * ) Notice: Subject to any disclaimer, the term of this patent is extended or adjusted under 35 U.S.C. 154(b) by 863 days.

(21) Appl. No.: 17/675,299

(22) Filed: Feb. 18, 2022

(65) Prior Publication Data

US 2022/0225972 A1    Jul. 21, 2022

Related U.S. Application Data

(63) Continuation of application No. 16/180,391, filed on Nov. 5, 2018, now Pat. No. 11,284,870.

(51) Int. Cl.
*A61B 10/02* (2006.01)

(52) U.S. Cl.
CPC .. *A61B 10/0275* (2013.01); *A61B 2010/0208* (2013.01); *A61B 10/0283* (2013.01)

(58) Field of Classification Search
CPC ............ A61B 10/0275; A61B 10/0283; A61B 2010/0208
See application file for complete search history.

(56) References Cited

U.S. PATENT DOCUMENTS

| | | | | |
|---|---|---|---|---|
| 4,678,459 A | * | 7/1987 | Onik | A61B 17/32002 604/22 |
| 5,334,159 A | * | 8/1994 | Turkel | A61B 17/3496 604/247 |
| 5,409,013 A | * | 4/1995 | Clement | A61M 39/223 600/566 |
| 5,423,330 A | * | 6/1995 | Lee | A61B 10/0283 606/166 |
| 9,456,808 B2 | | 10/2016 | Kapushion | |
| 9,585,639 B2 | | 3/2017 | Swick et al. | |
| 9,844,363 B2 | | 12/2017 | Wolton et al. | |

(Continued)

OTHER PUBLICATIONS

PCT International Search Report and Written Opinion for International Application. No. PCT/US2019/058574 , Applicant Hologic, Inc., dated Jan. 30, 2019 (13 pages).

(Continued)

*Primary Examiner* — Rene T Towa
(74) *Attorney, Agent, or Firm* — Jones Robb, PLLC

(57) ABSTRACT

A biopsy device includes a housing having a vacuum port, a cutter hub and attached cutter being slidably mounted in the housing so that the cutter hub and cutter are movable between a proximal, armed position, and a distal, fired position. A sealed cutter spring well with a cutter firing spring seated therein is disposed within the housing, wherein a proximal end of the cutter hub comprises a movable distal wall of the spring well so that proximal movement of the cutter hub compresses the cutter firing spring. A vacuum lumen is in communication with each of the vacuum port and spring well. A cutter arming valve assembly having a valve member is disposed in the vacuum lumen and selectively configurable to place the spring well in communication with the vacuum port for arming the cutter, or with atmosphere for firing the cutter.

20 Claims, 12 Drawing Sheets

(56) References Cited

U.S. PATENT DOCUMENTS

| | | |
|---|---|---|
| 10,022,110 B2 | 7/2018 | Stand, III et al. |
| 2003/0195436 A1 | 10/2003 | Van Bladel et al. |
| 2004/0049128 A1 | 3/2004 | Miller et al. |
| 2005/0049521 A1* | 3/2005 | Miller .................. A61B 10/025 600/565 |
| 2007/0106176 A1 | 5/2007 | Mark et al. |
| 2007/0239064 A1 | 10/2007 | Cicenas et al. |
| 2008/0103413 A1 | 5/2008 | Cicenas et al. |
| 2008/0300506 A1 | 12/2008 | McIntyre |
| 2017/0333012 A1 | 11/2017 | Hathaway |
| 2018/0103939 A1 | 4/2018 | Van Liere et al. |

OTHER PUBLICATIONS

Office Action in U.S. Appl. No. 16/180,391, dated Jul. 8, 2021.
Notice of Allowance from U.S. Appl. No. 16/180,391, dated Nov. 19, 2021.
Notice of Allowance from U.S. Appl. No. 16/180,391, dated Dec. 6, 2021.

* cited by examiner

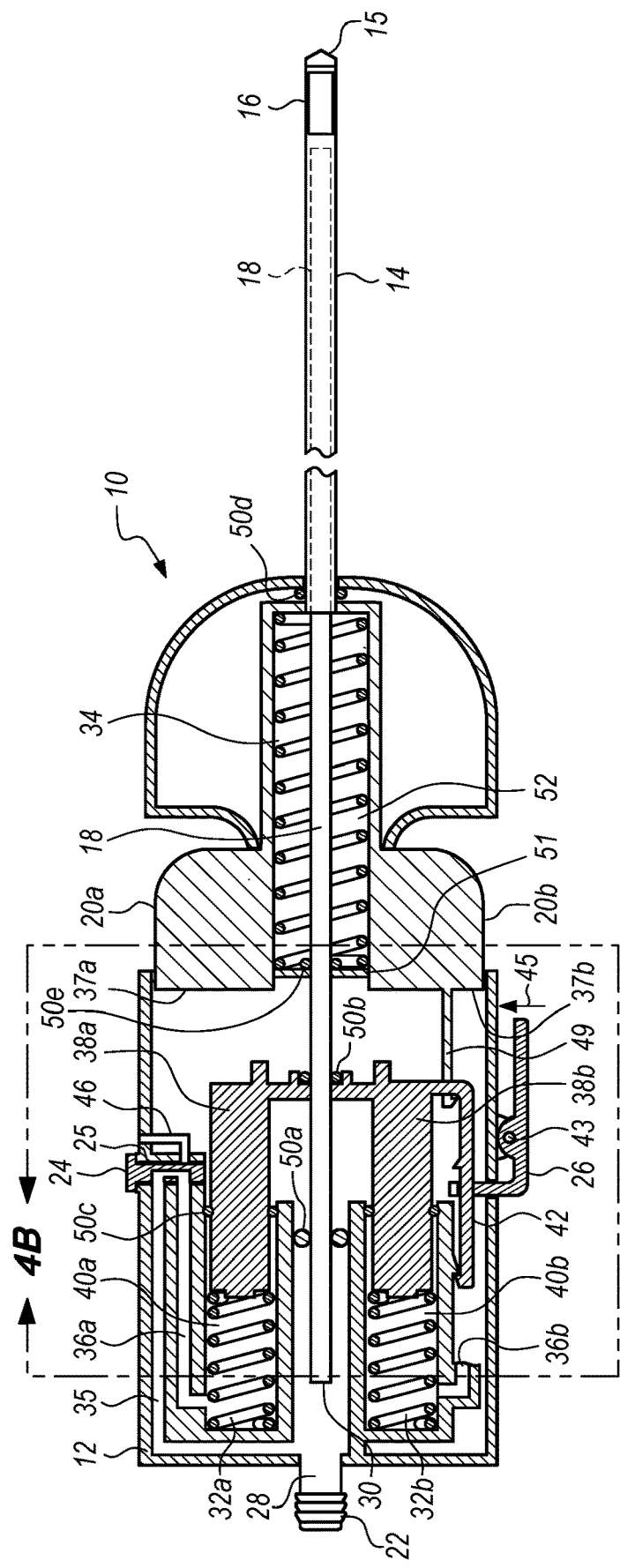

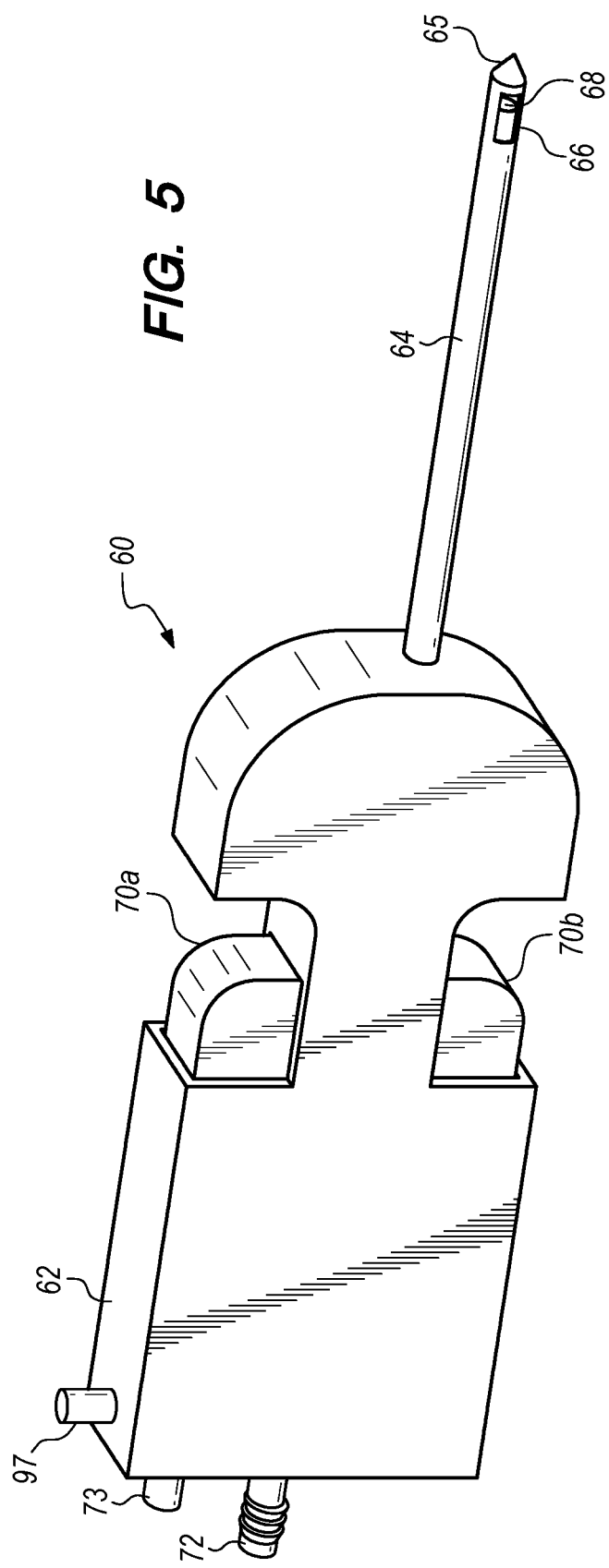

BIOPSY DEVICE

This application is a continuation application of U.S. patent application Ser. No. 16/180,391, filed Nov. 5, 2018, the entire contents of which are incorporated by reference herein.

FIELD

The present disclosure generally relates to the field of tissue sampling and harvesting. More specifically, the disclosure relates to biopsy needle sets and devices.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set. One known needle set includes an outer cannula having a pointed distal tip and a tissue receiving opening defined near its distal end, and an inner cannula having an open distal end surrounded by an annular cutting blade. The inner cannula is slidably disposed within the outer cannula so that it can close the tissue receiving opening, thereby cutting tissue prolapsing into the lumen of the outer cannula through the tissue receiving opening. Typically, a hub is connected to the proximal end of each needle. Such needle sets are used with or incorporated in various forms of biopsy devices, including single action, double action, and driven (e.g., by motors, etc.) biopsy devices.

Currently, there are several soft tissue biopsy devices that are classified as Spring-Loaded Core (SLC) biopsy devices. These all share the characteristics of employing springs to create force and movement in cannulas axially to selectively remove a sample of the tissue. These devices are required to have the springs loaded, or armed, manually to compress and lock the springs in a compressed state to prepare for actuating the device. As the device is actuated the cutter/inner cannula moves rapidly forward to cut through tissue adjacent to the needle/outer cannula and contain it within the inner cannula until it is retrieved by the clinician. Typically, SLC biopsy devices are handheld.

Some current biopsy devices utilize a vacuum to remove tissue samples from the inner cannula and are classified as Vacuum Assisted Breast Biopsy (VABB) devices.

Some vacuum assisted biopsy devices are table mounted and others are handheld. Mounting the biopsy device to a table can limit the ability of a user to move the device relative to the patient but can offer more precision. Handheld devices can be both technically easier to use and less expensive. Vacuum assisted biopsy devices include tethered and tether-less designs. Tethered vacuum assisted biopsy devices utilize external vacuum sources such as in-wall vacuum sources in clinical rooms. Tether-less vacuum assisted biopsy devices include mechanism for generating a vacuum such as motor driven pistons. Tethered vacuum assisted biopsy devices can restrict a clinician's movement during a biopsy, reducing effectiveness and increasing patient discomfort. Tether-less vacuum assisted biopsy device can be heavy or bulky (for handheld operation) due to the presence of vacuum generating mechanisms. Those vacuum generating mechanisms can also result in higher cost of the device.

Handheld devices, whether SLC devices or VABB devices, are desired to be used during ultrasound guided biopsy procedures, in which a physician operates the handheld biopsy device in one hand and the ultrasound transceiver in the other.

Biopsy devices may have single insertion, single core or single insertion, multiple core (SIMC) designs. Single insertion in both these designs refers to a single insertion of the needle/outer cannula during a biopsy procedure. In single sample designs, the cutter/inner cannula moves forward to cut through tissue adjacent to the needle/outer cannula once during a biopsy procedure. In multiple sample designs, the cutter/inner cannula moves forward to cut through tissue adjacent to the needle/outer cannula, then moves backward to rearm and allow the cutter/inner cannula to move forward again to cut through different tissue adjacent to the needle/outer cannula. The needle/outer cannula may be moved or rotated between samples to biopsy a different location in the tissue.

SUMMARY

For ultrasound procedures many physicians prefer to use SLC devices because they are easier to maneuver and are less costly than the vacuum assisted counterparts. Those physicians would prefer to use SLC devices to acquire multiple samples in a single insertion. However, many current SLC devices are deficient in that they are difficult for users to manually re-arm the inner cannula to acquire a second sample after the outer cannula has been inserted into a patient. Manually overcoming the spring force to re-arm the inner cannula may result in unintended movement of the device with the outer cannula in the patient, thereby causing the patient unnecessary discomfort. While electric motors may be incorporated to drive the inner and outer cannulas, biopsy devices having electric motors are more complicated and costlier than those without electric motors. Further, biopsy devices having electric motors are not amenable to cleaning and sterilization (e.g., with liquids and heat), which may damage various electrical connections and microprocessor controllers.

Various embodiments described and claimed herein overcome the above stated problems by providing a single insertion, multiple core device that allows for advantages of both a spring-loaded device and a vacuum assisted device. In one embodiment, a biopsy device includes an elongated housing having a vacuum port. The device also includes a cutter hub slidably mounted in and/or to the housing. The device further includes a cutter having a proximal portion coupled to the cutter hub, where the respective cutter hub and cutter are movable relative to the housing between a proximal, armed position, and a distal, fired position. Moreover, the device includes a sealed cutter spring well fixedly disposed within the housing. In addition, the device includes a cutter firing spring seated in the cutter spring well, where proximal movement of the cutter hub relative to the housing compresses the cutter firing spring. The device also includes a vacuum lumen in communication with each of the vacuum port and the cutter spring well. The device further includes a cutter arming valve assembly having a valve member disposed in or adjacent to the vacuum lumen, where the cutter arming valve assembly is selectively configurable to place the cutter spring well in communication with the vacuum port via the vacuum lumen for arming the cutter, or in communication with atmosphere for firing the cutter.

In one or more embodiments, the cutter hub includes or is otherwise attached to a cutter arming latch configured to engage a cutter retention catch that is fixed relative to the housing to thereby retain the cutter hub and the cutter, respectively, in the armed position, where the cutter firing spring is in a compressed configuration when the cutter hub and the cutter are in the armed position. The device may also include a firing mechanism operatively coupled to the cutter arming latch such that actuation of the firing mechanism disengages the cutter arming latch from the cutter retention catch to allow the cutter firing spring to restore from the compressed configuration to an uncompressed configuration when the cutter arming valve assembly is configured to place the cutter spring well in communication with atmosphere.

In one or more embodiments, the device also includes a needle hub slidably mounted in and/or to the housing. The device further includes a needle having a lumen and proximal end portion coupled to the needle hub, where the respective needle hub and needle are movable relative to the housing between a proximal, armed position, and a distal, fired position, and where a distal portion of the cutter is slidably disposed in the needle lumen. Moreover, the device includes a needle spring well fixedly disposed within the housing. In addition, the device includes a needle firing spring seated in the needle spring well, where a proximal end portion of the needle hub includes, or is attached to, a movable distal end wall of the needle spring well so that proximal movement of the needle hub relative to the housing compresses the needle firing spring.

In one or more embodiments, the needle includes a closed, tissue penetrating distal end, and a side tissue resection window disposed in a distal portion of the needle. The needle hub may include or be otherwise attached to a needle arming member moveably mounted in and/or to the housing, the needle arming member configured for manually-actuated movement from a relaxed, extended position to a loaded, compressed position to define a compressive needle arming stroke. The needle hub and the cutter hub may be configured such that manually actuating the needle arming member moves the cutter hub and the cutter into the armed position and compresses the cutter firing spring.

In one or more embodiments, the device also includes a needle retention latch that engages the cutter retention catch. The outer cannula hub may include, or be otherwise attached to, the needle retention latch having a needle catch at a proximal end thereof configured to engage an outer cannula retention catch disposed on, or otherwise attached to, the cutter arming latch to thereby retain the outer cannula hub and outer cannula, respectively, in an armed position, where the outer cannula firing spring is in a compressed configuration when the outer cannula is in the armed configuration. Actuation of the firing mechanism may disengage the outer cannula arming latch from the outer cannula retention catch in order to fire the respective outer cannula hub and outer cannula distally relative to the housing due to the outer cannula firing spring restoring from the compressed configuration to an uncompressed configuration, in which the outer cannula is in a fired position. A proximal end portion of the cutter hub may include, or be otherwise attached to, a movable distal end wall of the cutter spring well.

In another embodiment, a method for tissue biopsy includes moving a needle from a distal fired position within an elongate housing to a proximal armed position, thereby compressing a needle firing spring within a needle firing spring chamber. The method also includes moving a cutter slidably and coaxially disposed in the needle from a distal fired position to a proximal armed position, thereby compressing a cutter firing spring within a cutter firing spring chamber. The needle and/or the cutter are moved to their respective proximal armed positions by a vacuum provided through a vacuum port in the elongated housing, where the vacuum generates sufficient force to compress the needle firing spring and/or the cutter firing spring.

In one or more embodiments, the method also includes actuating a firing mechanism to release the compressed needle firing spring and the compressed cutter firing spring to allow the compressed needle firing spring and the compressed cutter firing spring to move the needle and the cutter from respective proximal armed positions to respective fired positions. Actuating the firing mechanism may redirect the vacuum from the needle firing spring chamber and the cutter firing spring chamber to a needle firing assist chamber and a cutter firing assist chamber, respectively.

In still another embodiment, a biopsy device includes a housing having a vacuum port. The device also includes an outer cannula having a lumen and a tissue penetrating distal end, where a proximal end portion of the outer cannula is movably coupled to the housing, a distal portion of the outer cannula having a having a side tissue resection window. The device further includes a cutter having a distal portion slidably disposed in the outer cannula lumen, where the cutter is movably coupled to the housing, and where a proximal portion of the cutter extends out of a proximal end opening of the outer cannula. Moreover, the device includes an outer cannula firing member movably disposed in said housing, where a proximal end portion of the outer cannula is coupled to the outer cannula firing member. In addition, the device includes a cutter firing member movably disposed in said housing, where a proximal portion of the cutter is coupled to the cutter firing member. The device also includes an outer cannula firing spring seated in an outer cannula firing spring chamber within the housing, where proximal movement of the outer cannula firing member relative to the housing compresses the outer cannula firing spring. The device further includes a first cutter firing spring seated in a first cutter firing spring chamber within the housing, Moreover, the device includes a second cutter firing spring seated in a second cutter firing spring chamber within the housing, where proximal movement of the cutter firing member relative to the housing compresses the first and second cutter firing springs. In addition, the device includes a cutter vacuum lumen that is in fluid communication with each of the vacuum port, the first cutter firing spring chamber and the second cutter firing spring chamber. The method also includes a cutter arming valve member movably disposed in the cutter vacuum lumen and configured to selectively simultaneously place the first and second cutter firing spring chambers in communication with the vacuum port or to simultaneously isolate the first and second cutter firing spring chambers from the vacuum port.

In one or more embodiments, the cutter firing member includes or is otherwise attached to a cutter arming latch configured to engage a cutter retention catch that is fixed relative to the housing to thereby retain the cutter firing member and the cutter, respectively, in a proximal armed position, where the cutter firing spring is in a compressed configuration when the cutter hub and the cutter are in the armed position. The device may also include a firing mechanism operatively coupled to the cutter arming latch such that actuation of the firing mechanism disengages the cutter arming latch from the cutter retention catch to allow the cutter firing spring to restore from the compressed configuration to an uncompressed configuration when the cutter arming valve member is configured to place the cutter spring well in communication with atmosphere.

In one or more embodiments, the outer cannula firing member includes or is otherwise attached to an outer cannula arming member moveably mounted in and/or to the housing, the outer cannula firing member configured for manually-actuated movement from a relaxed, extended position to a loaded, compressed position to define a compressive arming stroke. The outer cannula firing member and the cutter firing member may be configured such that manually actuating the outer cannula firing member moves the cutter firing member and the cutter into a proximal armed position and compresses the cutter firing spring. The device may also include an outer cannula retention latch that engages the cutter retention latch. The outer cannula firing member may include, or be otherwise attached to, the outer cannula retention latch having an outer cannula catch at a proximal end thereof configured to engage an outer cannula retention catch disposed on, or otherwise attached to, the cutter arming latch to thereby retain the outer cannula firing member and outer cannula, respectively, in an armed position, where the outer cannula firing spring is in a compressed configuration when the outer cannula is in the armed configuration.

In one or more embodiments, actuation of the firing mechanism disengages the outer cannula arming latch from the outer cannula retention catch in order to fire the respective outer cannula firing member and outer cannula distally relative to the housing due to the outer cannula firing spring restoring from the compressed configuration to an uncompressed configuration, in which the outer cannula is in a fired position. The outer cannula firing member may form a distal end wall of the outer cannula firing spring chamber. Respective portions of the cutter firing member may form respective distal end walls of the first and second cutter firing spring chambers.

In yet another embodiment, a biopsy device includes a housing having a vacuum port. The device also includes an outer cannula having a lumen and a tissue penetrating distal end, where a proximal end portion of the outer cannula is movably coupled to the housing, a distal portion of the outer cannula having a side tissue resection window. The device further includes a cutter having a distal portion slidably disposed in the outer cannula lumen, where the cutter is movably coupled to the housing, and where a proximal portion of the cutter extends out of a proximal end opening of the outer cannula. Moreover, the device includes an outer cannula firing member movably disposed in said housing, where a proximal end portion of the outer cannula is coupled to the outer cannula firing member. In addition, the device includes a cutter firing member movably disposed in said housing, where a proximal portion of the cutter is coupled to the cutter firing member. The device also includes an outer cannula firing spring seated in an outer cannula firing spring chamber within the housing, where proximal movement of the outer cannula firing member relative to the housing compresses the outer cannula firing spring. The device further includes a cutter firing spring seated in a cutter firing spring chamber within the housing, where proximal movement of the cutter firing member relative to the housing compresses the cutter firing spring. Moreover, the device includes an outer cannula vacuum lumen in fluid communication with the vacuum port and the outer cannula firing spring chamber. In addition, the device includes a cutter vacuum lumen in fluid communication with the vacuum port and the cutter firing spring chamber. The device also includes an outer cannula arming valve disposed adjacent the outer cannula vacuum lumen and configured to selectively place the outer cannula firing spring chamber in communication with the vacuum port or to isolate the outer cannula firing spring chamber from the vacuum port. The device further includes a cutter arming valve disposed adjacent the cutter vacuum lumen and configured to selectively place the cutter firing spring chamber in communication with the vacuum port or to isolate the cutter firing spring chamber from the vacuum port.

In one or more embodiments, the device also includes an outer cannula firing assist chamber within the housing, where the outer cannula firing member forms a proximal end wall of the outer cannula firing assist chamber. The device further includes a cutter firing assist chamber within the housing, where the cutter firing member forms a proximal end wall of the cutter firing assist chamber. Moreover, the device includes a firing assist vacuum lumen that is in fluid communication with each of the vacuum port, the outer cannula firing assist chamber, and the cutter firing assist chamber. In addition, the device includes a firing assist valve disposed adjacent the firing assist vacuum lumen and configured to selectively place the outer cannula firing assist chamber and the cutter firing assist chamber in communication with the vacuum port or to isolate the outer cannula firing assist chamber and the cutter firing assist chamber from the vacuum port.

In one or more embodiments, the device also includes an outer cannula vent valve disposed adjacent the outer cannula vacuum lumen and configured to selectively place the outer cannula firing spring chamber in communication with an atmosphere or to isolate the outer cannula firing spring chamber from the atmosphere. The device further includes a cutter vent valve disposed adjacent the cutter vacuum lumen and configured to selectively place the cutter firing spring chamber in communication with the atmosphere or to isolate the cutter firing spring chamber from the atmosphere. Moreover, the device includes a firing assist vent valve disposed adjacent the firing assist vacuum lumen and configured to selectively place the outer cannula firing assist chamber and the cutter firing assist chamber in communication with the atmosphere or to isolate the outer cannula firing assist chamber and the cutter firing assist chamber from the atmosphere. The outer cannula firing member may form a distal end wall of the outer cannula firing spring chamber. The cutter firing member may form a distal end wall of the cutter firing spring chamber.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIG. 4A is a side cross-sectional view of the biopsy device depicted in FIG. 1 in a partially armed configuration.

FIG. 5 is a perspective view of a biopsy device, according to some embodiments.

DETAILED DESCRIPTION OF THE ILLUSTRATED EMBODIMENTS

As described above, with a single insertion, single core spring-loaded needle biopsy device, the needle/outer cannula may be manually re-inserted multiple times to take multiple samples. Re-inserting the needle/outer cannula can cause additional pain and scarring for the patient. Such manual manipulation can cause fatigue for the physician operating the device and increase the procedure time if multiple cores are obtained. Similarly, with a manually operated single insertion, multiple core spring-loaded needle biopsy device, the cutter/inner cannula may be manually re-armed before taking each sample. Manually overcoming the spring that fires the cutter/inner cannula can cause fatigue for the physician operating the device and increase the procedure time and discomfort for the patient. Various embodiments described and claimed herein overcome the above stated problems by providing a single insertion, multiple core device that allows for advantages of both a spring-loaded device and a vacuum assisted device. The devices described herein can be attached to a vacuum source, such an in-wall vacuum source or a standing vacuum source which can be found in a procedure room.

Vacuum Assisted and Spring-Loaded Core Biopsy Device Embodiment 1

Vacuum assisted and spring-loaded core biopsy devices described herein can operate in at least some of three firing modes: sequential, individual and cyclical. In sequential firing mode (Embodiments 1 and 2), the inner and outer cannulas are fired in rapid succession to advance into the target area and acquire the tissue through a single user input. In individual firing mode (Embodiment 2), the inner and outer cannulas are fired individually to allow the user to control the timing of the rapid advancement of the cannulas. In cyclical firing mode (Embodiment 2), the outer cannula is rapidly advanced to the target location, followed by rapid advancement of the inner cannula. After completion of the advancement of the inner cannula, the inner cannula is re-armed, and rapidly advanced another time. This is repeated until the user releases an actuator. This allows multiple cores to be acquired with a single insertion of the device.

Figure 1:
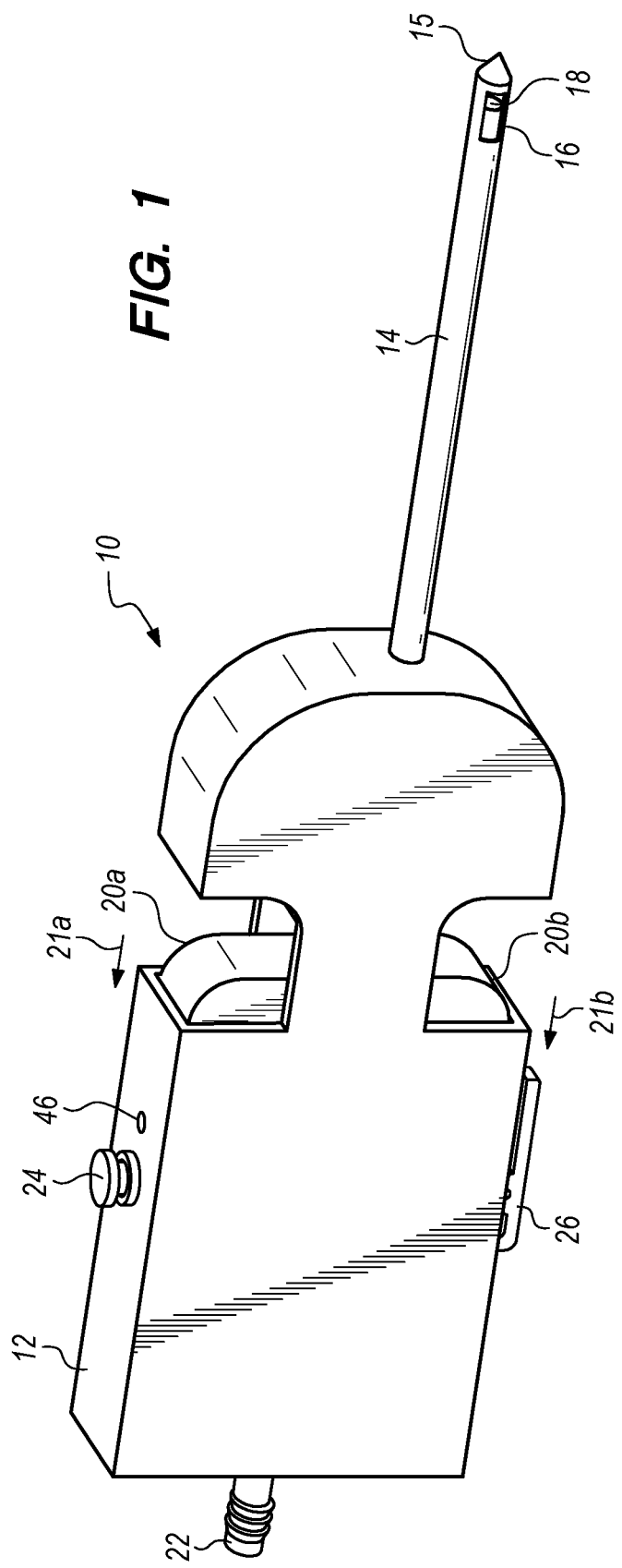
FIG. 1 is a perspective view of a biopsy device, according to some embodiments.

FIG. 1 depicts a vacuum assisted and spring-loaded core biopsy device 10 according to some embodiments. The springs 32a, 32b, 34 in the biopsy device 10 provide the force for rapid advancement of the inner and outer cannulas 18, 14. The vacuum port 22 allows connection to an external vacuum for arming the inner cannula 18 and moving excised samples through the inner cannula 18. Having vacuum assistance allows the inner cannula 18 to be armed when the outer cannula 14 is in the patient while minimizing force exerted on the device 10 and movement of the device 10 in the patient.

The device 10 includes a housing 12, an outer cannula/needle 14 slidably disposed in the housing 12, and an inner cannula/cutter 18 coaxially and slidably disposed in the outer cannula 14. The outer cannula 14 has a sharpened distal end 15 and defines a side window 16 at the distal end thereof. The inner cannula 18 has an open distal end at least partially defined by a sharpened (e.g., annular) cutting surface. The device 10 also includes a pair of sliders/needle hubs 20a, 20b configured to manually arm the outer and inner cannulas 14, 18 to perform a biopsy using the device 10. The device 10 further includes an aspiration/vacuum port 22, a port for an atmosphere vent 46, and inner cannula vacuum arming valve 24, and an actuator/firing mechanism 26.

In operation, the device 10 may be coupled to an aspiration/vacuum source (not shown) via the aspiration/vacuum port 22. A user may manually move the sliders 20a, 20b in a proximal direction 21a, 21b (e.g., by squeezing with index and middle fingers of a hand) to compress a plurality of springs to arm the outer and inner cannulas 14, 18, thereby placing the device 10 in a fully armed configuration, as described below. Next, the user may place the sharpened distal end 15 of the outer cannula 14 against the skin of a patient and depress the actuator 26 to fire the outer and inner cannulas 14, 18 partially into tissue of the patient. Firing the outer and inner cannulas 14, 18 places the device 10 in a fully fired configuration, as described below.

The user may then depress the inner cannula vacuum arming valve 24 in direction 27 to arm the inner cannula 18, thereby placing the device 10 in a partially armed configuration, as described below. With the device 10 in the partially armed configuration, the inner cannula 18 is withdrawn proximally relative to the outer cannula 14, which at least partially opens the side window 16 in the outer cannula 14. The vacuum exerted through the inner cannula 18 draws tissue through the side window 16 and into an interior of the outer cannula 14.

Next, the user may again depress the actuator 26 to fire the inner cannula 18 across the side window 16 in the outer cannula 14 and the tissue (not shown) extending therethrough. As the inner cannula 18 is fired across the tissue, the sharpened cutting surface at the open distal end of the inner cannula 18 separates the tissue from the patient and deposits the separated tissue sample in an interior of the inner cannula 18. The vacuum exerted through the inner cannula 18 draws the separated tissue sample proximally down the inner cannula 18 and into a collection area (not shown). In some embodiments, the collection area may be a removable cartridge or a plurality of removable cartridges in the proximal end of the device 10 and removably coupled to the proximal end 30 of the inner cannula 18. The cartridge(s) may be removed from the device 10 through a door after tissue collection. In other embodiments, the collection area may be one or more tissue traps disposed outside of the device 10 and removably coupled between the aspiration/vacuum port 22 and the vacuum source. The sample(s) may be removed from the tissue trap after tissue collection. Firing the inner cannula 18 places the device 10 in a fully fired configuration, as described below. The user may continue to alternately depress the inner cannula vacuum arming valve 24 and the actuator 26 to re-arm and fire the inner cannula 18 to serially collect a plurality of separated tissue samples with minimal movement of the device 10, thereby minimizing unnecessary discomfort for the patient. The user may rotate, or otherwise minimally move, the device before each re-arming and firing cycle to collect a plurality of separated tissue samples from the slightly different areas of the patient.

Figure 2A:
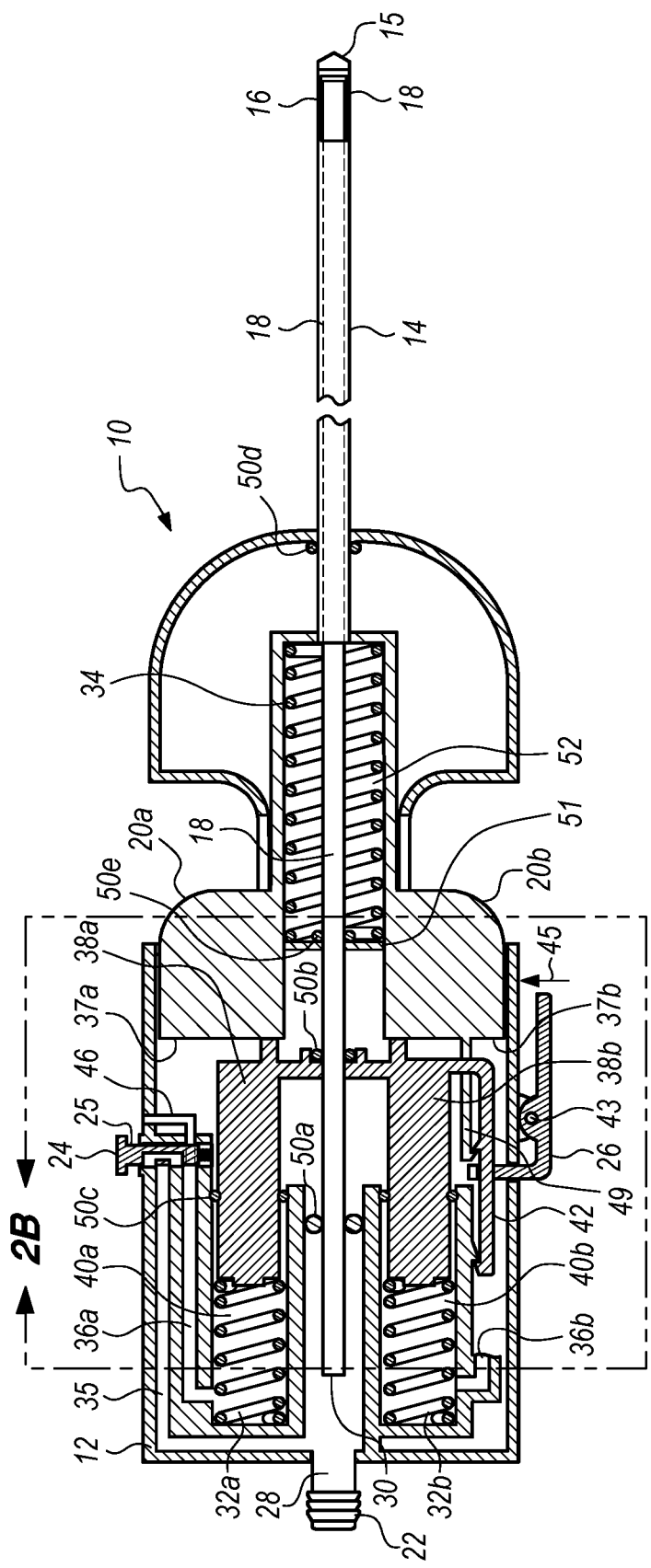
FIG. 2A is a side cross-sectional view of the biopsy device depicted in FIG. 1 in a fully armed configuration.
Figure 2B:
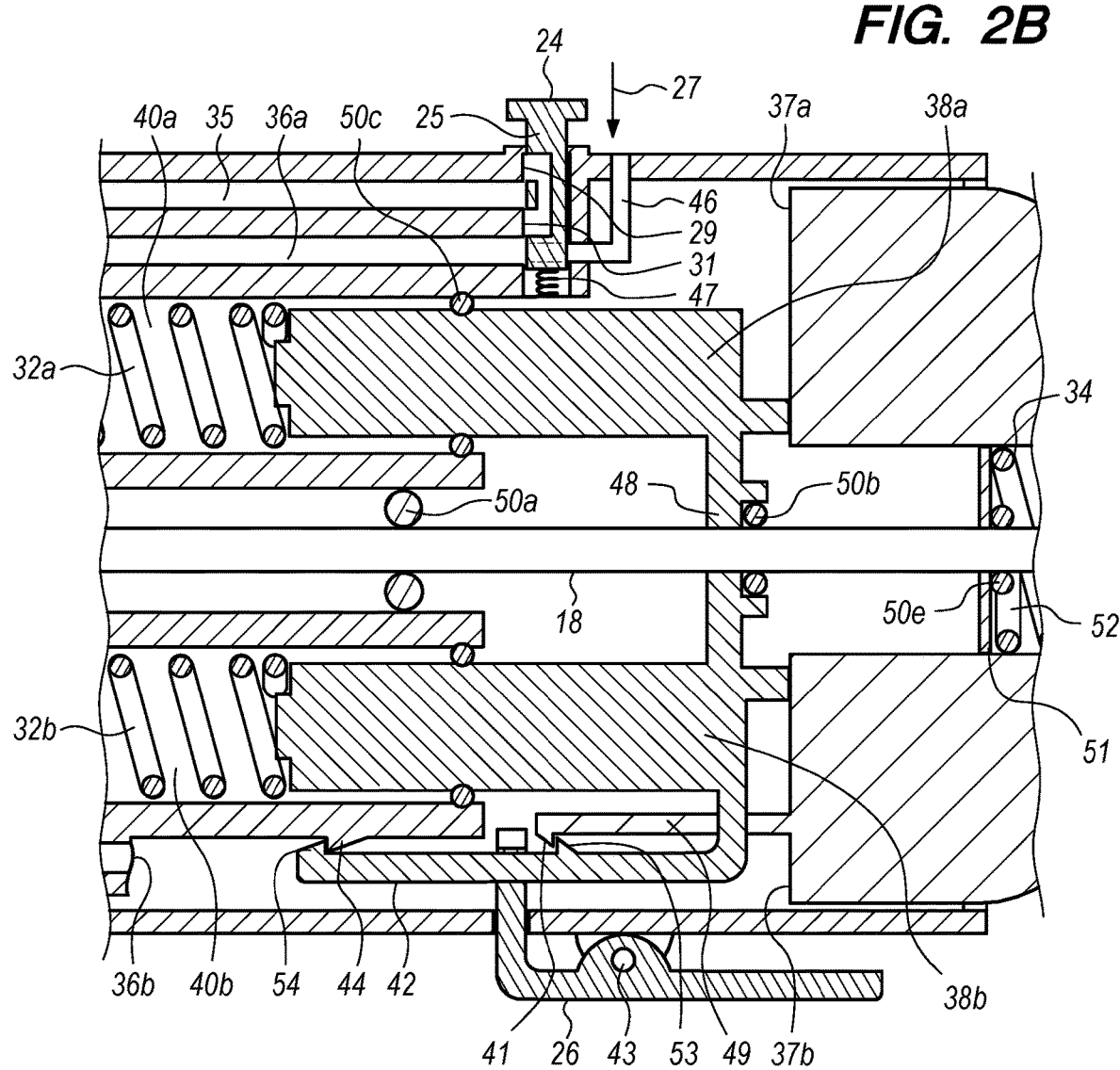
FIG. 2B is a detailed side cross-sectional view of the biopsy device depicted in FIG. 1 in a fully armed configuration.

FIGS. 2A and 2B depict in cross-section and detailed cross-section the vacuum assisted and spring-loaded core biopsy device 10 depicted in FIG. 1. FIG. 2A depicts the device 10 in the fully armed configuration with the outer and inner cannulas 14, 18 and the sliders 20*a*, 20*b* in proximal positions. The sliders 20*a*, 20*b* are coupled to the outer cannula 14 and defined an outer cannula spring chamber/well 52 that contains an outer cannula spring 34. The outer cannula spring chamber 52 is also defined by a flange 51 at a proximal end thereof. The flange 51 is coupled to the biopsy device housing 12. The sliders 20*a*, 20*b* are movable relative to the flange 51 to reduce the length of the outer cannula spring chamber 52 and compress the outer cannula spring 34 contained therein. With the device 10 in the fully armed configuration depicted in FIG. 2A, the sliders 20*a*, 20*b* are in their proximal positions thereby compressing the outer cannula spring 34 to arm the outer cannula 14 for firing.

In the fully armed configuration depicted in FIG. 2A, the sliders 20*a*, 20*b* are disposed adjacent respective spring compression members//cutter hubs 38*a*, 38*b* such that moving the sliders 20*a*, 20*b* proximally exerts a proximally directed force on the spring compression members 38*a*, 38*b* through the respective proximal surfaces 37*a*, 37*b* of the sliders 20*a*, 20*b*. The proximally directed force has moved the spring compression members 38*a*, 38*b* proximally, thereby respectively compressing inner cannulas springs 32*a*, 32*b*, which are respectively disposed in inner cannula spring chambers/wells 40*a*, 40*b*. The spring compression members 38*a*, 38*b* are also coupled to the inner cannula 18 at a yoke 48, such that moving the spring compression members 38*a*, 38*b* proximally also moves the inner cannula 18 proximally. With the spring compression members 38*a*, 38*b* and the inner cannula 18 in proximal positions, and with the inner cannulas springs 32*a*, 32*b* compressed, the inner cannula 18 is armed for firing.

The sliders 20*a*, 20*b* are coupled to a needle retention/outer cannula latch 49 having an outer cannula catch 41. The spring compression members 38*a*, 38*b* are coupled to an inner cannula/cutter arming latch 42 having a needle retention/distal catch 53 and a proximal catch 54. The inner cannula latch 42 is operatively coupled to the actuator 26. The biopsy device housing 12 is coupled to a housing catch/cutter retention catch 44. The outer cannula catch 41 is configured to slide proximally past the distal catch 53 to removably couple the sliders 20*a*, 20*b* and the spring compression members 38*a*, 38*b* together so that they can be fired together from the fully armed configuration depicted in FIGS. 2A and 2B to the fully fired configuration depicted in FIG. 3 and described below. Similarly, the proximal catch 54 is configured to slide proximally past the housing catch 44 to arm the spring compression members 38*a*, 38*b* and the inner cannula 18 coupled thereto in the armed proximal position. When the outer cannula catch 41/distal catch 53 and the proximal catch 54/housing catch 44 pairs are both engaged, releasing the proximal catch 54 from the housing catch 44 by depressing the actuator 26 in direction 45 releases both the sliders 20*a*, 20*b* and the spring compression members 38*a*, 38*b*, allowing the outer and inner cannulas 14, 18 to be fired together. When the outer cannula catch 41/distal catch 53 are disengaged and the proximal catch 54/housing catch 44 are engaged, releasing the proximal catch 54 from the housing catch 44 by depressing the actuator 26 releases the spring compression members 38*a*, 38*b* and the inner cannula 18 to be fired.

The device 10 also includes a plurality of O-rings 50*a*, 50*b*, 50*c*, 50*d*, 50*e* to form fluid tight seals between various moving components of the device 10. O-ring 50*a* forms a fluid tight seal between the inner cannula 18 and the portions of the housing 12 defining the inner cannula spring chambers 40*a*, 40*b*. O-ring 50*b* forms a fluid tight seal between the inner cannula 18 and the yoke 48 of the spring compression members 38*a*, 38*b*. O-rings 50*c* form fluid tight seals between the spring compression members 38*a*, 38*b* and the portions of the housing 12 defining the inner cannula spring chambers 40*a*, 40*b*. O-ring 50*d* forms a fluid tight seal between the outer cannula 14 and the housing 12. O-ring 50*e* forms a fluid tight seal between the inner cannula 18 and the flange 51. These fluid tight seals maintain vacuums that are generated in the inner cannula spring chambers 40*a*, 40*b*, and minimize contamination of the interior of the device 10 with liquids that may be withdrawn into the device 10 along with the separated tissue sample.

The device 10 further includes a pneumatic system for re-arming the inner cannula 18 as described above. The pneumatic system includes an aspiration/vacuum port 22, which leads to a lumen 28 extending through the housing 12 of the device adjacent the open proximal end 30 of the inner cannula 18. The lumen 28 is fluidly coupled to a first vacuum lumen 35, which ends at a valve body 25 of an inner cannula arming valve 24. The valve body 25 includes first and second valve openings 29, 31 that are fluidly coupled to each other. The valve body 25 of the inner cannula arming valve 24 is also adjacent to second vacuum lumens 36*a* and 36*b*, which are fluidly coupled to inner cannula spring chambers 40*a*, 40*b* respectively. The valve body 25 is also adjacent to the atmosphere vent 46 the selectively couples to the second valve lumens 36*a*, 36*b*. Under the valve body 25 is disposed a biasing spring 47, that biases the inner cannula arming valve 24 in a closed position.

In FIGS. 2A and 2B, the inner cannula arming valve 24 is in the closed position due to an unopposed upward force exerted by the biasing spring 47. Accordingly, the valve body 25 of the inner cannula arming valve 24 is obstructing the first and second vacuum lumens 35, 36*a*, 36*b*. As a result, any vacuum delivered through the aspiration/vacuum port 22 and the lumen 28 through housing 12 will not reach the inner cannula spring chambers 40*a*, 40*b*. In addition, the atmosphere vent 46 is coupled to the second valve lumens 36*a*, 36*b*, thereby allowing any vacuum in the inner cannula spring chambers 40*a*, 40*b* to vent to atmosphere. With the inner cannula arming valve 24 in the closed position depicted in FIGS. 2A and 2B, any vacuum in or connected to the device 10 plays no role in the arming or firing of the inner cannula 18. Instead, the inner cannula 18 has been manually armed by a user depressing the sliders 20*a*, 20*b* as described above.

Figure 3A:
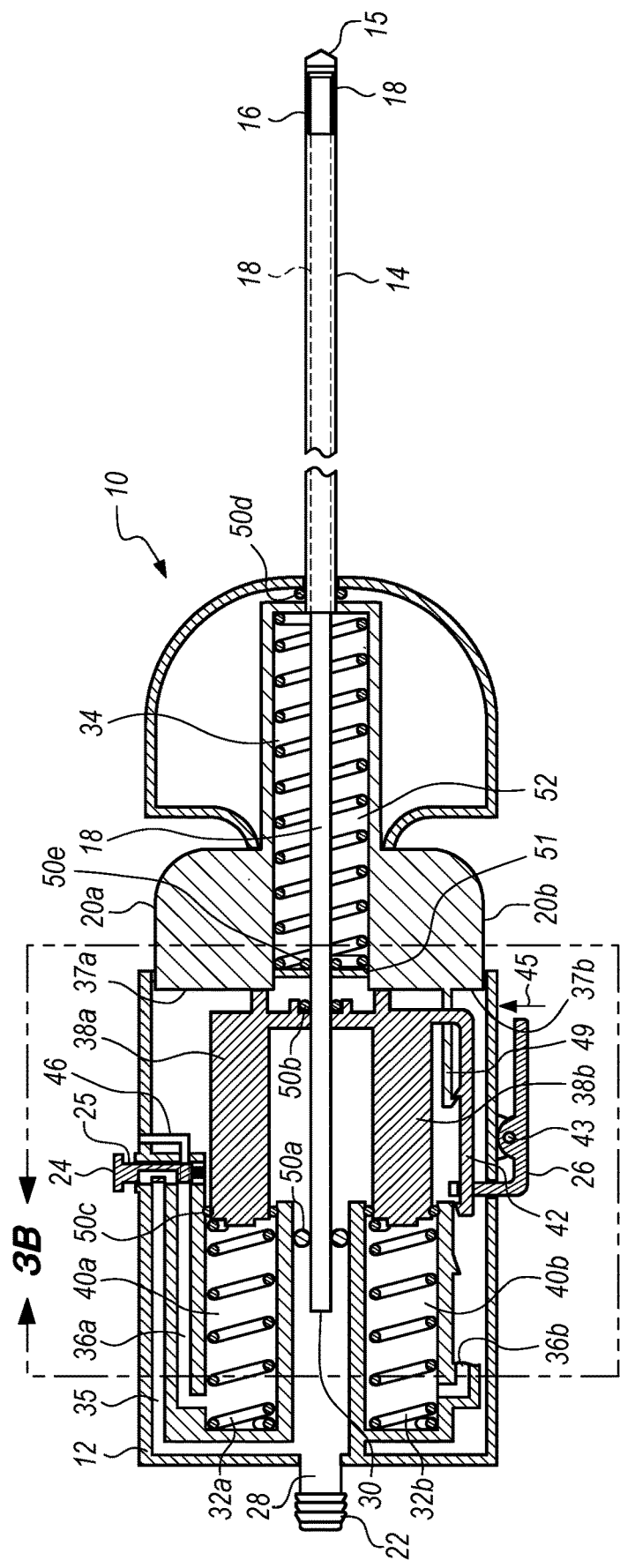
FIG. 3A is a side cross-sectional view of the biopsy device depicted in FIG. 1 in a fully fired configuration.

FIG. 3A depicts the biopsy device 10 depicted in FIG. 1 in a fully fired configuration. A user may trigger the device 10 to fire by depressing the distal end of the actuator 26, which causes the actuator 26 to pivot about the pin 43 that mounts the actuator 26 to the body 12. Movement of the actuator 26 in turn, moves the inner cannula latch 42 away from the housing catch 44, resulting in the proximal catch 54 disengaging from the housing catch 44 and the distal catch 53 disengaging from the outer cannula catch 41. Disengaging the proximal catch 54 from the housing catch 44 and the distal catch 53 disengaging from the outer cannula catch 41 allows the inner cannula springs 32a, 32b, and the outer cannula spring 34, which were all compressed in the fully armed configuration depicted in FIGS. 2A and 2B, to expand and fire the outer and inner cannulas 14, 18 distally. This firing transforms the device 10 from the fully armed configuration depicted in FIGS. 2A and 2B to the fully fired configuration depicted 3A and 3B.

In some embodiments, when the device 10 is fired by depressing the actuator 26, the proximal catch 54 and the housing catch 44 are disengaged from each other, but the distal catch 53 may remain engaged with the outer cannula catch 41. This ensures that the outer and inner cannulas 14, 18 will fire as one unit with the window 16 in the outer cannula 14 closed by the inner cannula 18.

In the fully fired configuration, the inner cannula arming valve 24 remains in the closed position due to an unopposed upward force exerted by the biasing spring 47. Accordingly, any vacuum in or connected to the device 10 plays no role in the arming or firing of the inner cannula 18 in the fully fired configuration as described above for the fully armed configuration.

FIG. 4A depicts the biopsy device 10 depicted in FIG. 1 in a partially armed configuration. A user may trigger the device 10 to armed the inner cannula 18 using a vacuum by depressing the inner cannula arming valve 24 while depressing (to a greater extent compared to actuating the device to fire as described above) and holding the distal end of the actuator 26. Depressing the distal end of the actuator 26 a greater extent causes the actuator 26 to pivot a greater extent about the pin 43 that mounts the actuator 26 to the body 12. This greater movement of the actuator 26 in turn, moves the inner cannula latch 42 further away from the housing catch 44, resulting in the distal catch 53 disengaging from the outer cannula catch 41. Disengaging the distal catch 53 from the outer cannula catch 41 allows the spring compression members 37a, 37b to be separated from the sliders 20a, 20b.

While continuing to hold the depressed actuator 26, which continues to disengage the distal catch 53 from the outer cannula catch 41, the user depresses the inner cannula arming valve 24. Depressing the inner cannula arming valve 24 overcomes the upward force exerted by the biasing spring 47, thereby opening the inner cannula arming valve 24. With the inner cannula arming valve 24 in the open position shown in FIG. 4B, the first valve opening 29 is fluidly coupled to the first vacuum lumen 35 and the second valve opening 31 is fluidly coupled to the second vacuum lumens 36a, 36b. Further, with the inner cannula arming valve 24 in the open position shown in FIG. 4B, the valve body 25 includes the atmosphere vent 46. Coupling the first and second vacuum lumens 35, 36a, 36b via the valve body 25 and occluding the atmosphere vent 46 fluidly couples any vacuum applied at the aspiration/vacuum port 22 to the inner cannula spring chambers 40a, 40b. The vacuum force applied at the aspiration/vacuum port 22 and the inner cannula springs 32a, 32b are configured such that the vacuum pulls the spring compression members 38a, 38b proximally to compress the inner cannula springs 32a, 32b and move the inner cannula 18 proximally. As described above, moving the inner cannula 18 proximally opens the window 16 in the outer cannula 14 to allow the vacuum to draw tissue into the interior of the outer cannula through the open window 16 to be separated and sampled.

Figure 3B:
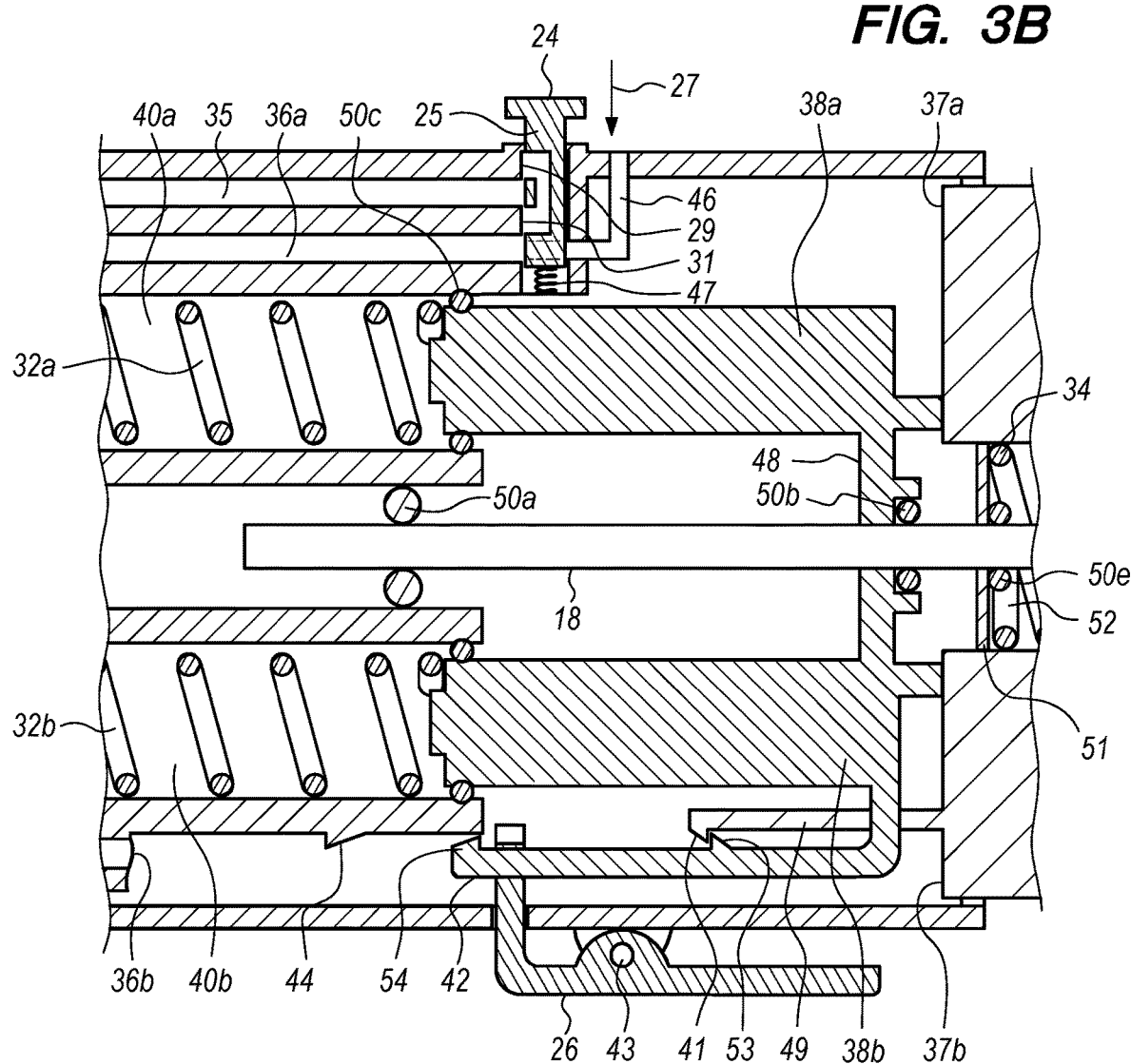
FIG. 3B is a detailed side cross-sectional view of the biopsy device depicted in FIG. 1 in a fully fired configuration.
Figure 4B:
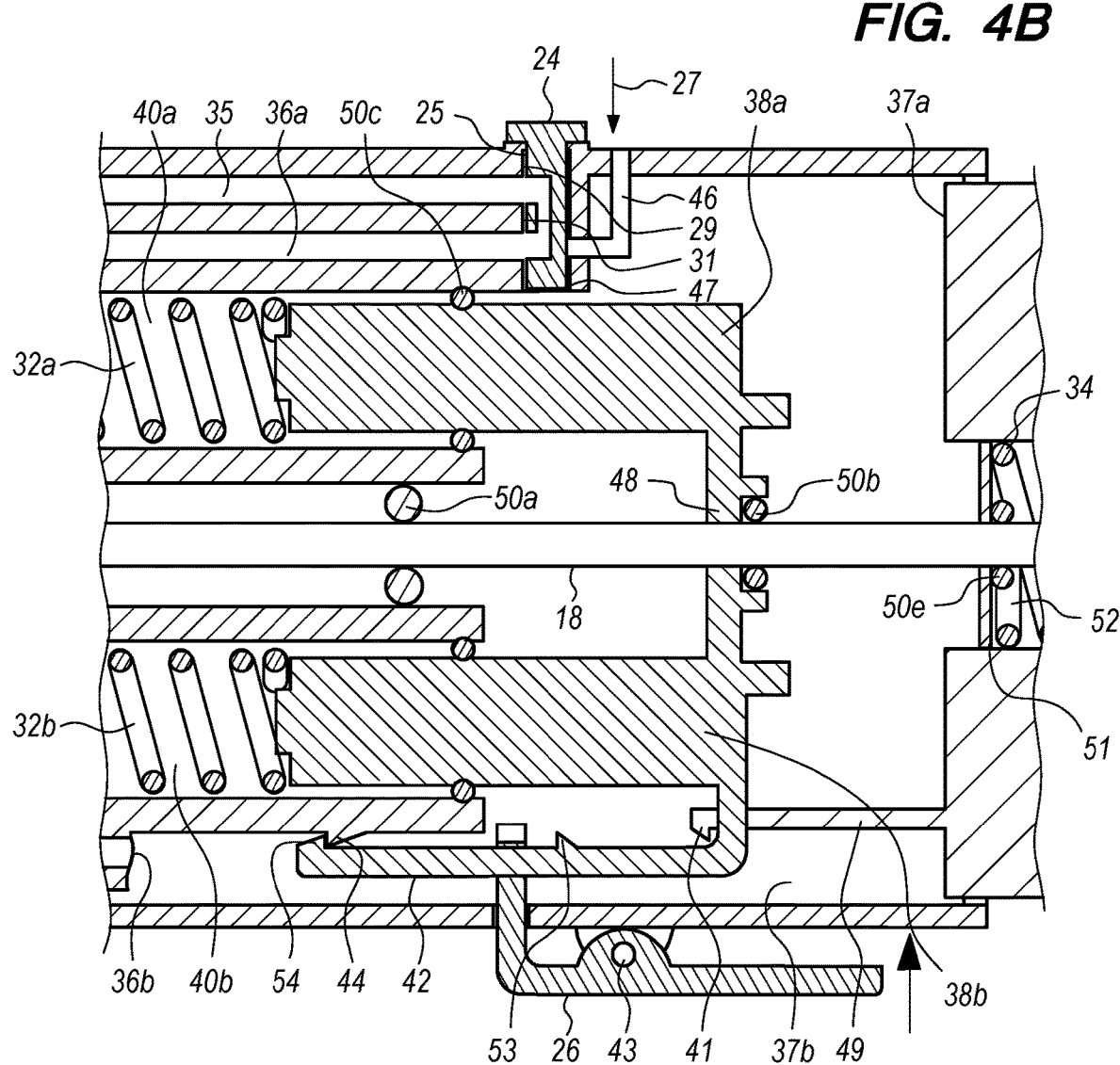
FIG. 4B is a detailed side cross-sectional view of the biopsy device depicted in FIG. 1 in a partially armed configuration.

After the vacuum has drawn the spring compression members 38a, 38b proximally to compress the inner cannula springs 32a, 32b and move the inner cannula 18 proximally, the user may release the actuator 26, which is biased to return to the position depicted in FIG. 4B. In the firing actuator 26 position depicted in FIG. 4B, the proximal catch 54 and the housing catch 44 are engaged with each other, while the distal catch 53 remains disengaged from the outer cannula catch 41. This moves the device 10 from the fully fired configuration depicted in FIGS. 3A and 3B to the partially armed configuration depicted in FIGS. 4A and 4B, in which the inner cannula 18 is armed and ready to be fired.

In order to fire the inner cannula 18 with the device 10 in the partially armed configuration depicted in FIGS. 4A and 4B, the user may depress the distal end of the actuator 26 as described above for the transition from the fully armed configuration depicted in FIGS. 2A and 2B to the fully fired configuration depicted in FIGS. 3A and 3B. Firing the inner cannula 18 with the device 10 in the partially armed configuration results in the fully fired configuration depicted in FIGS. 3A and 3B.

As described above, before moving the device 10 from the fully fired configuration to the partially armed configuration, the user can manipulate the device 10 to move the window 16 in the patient's tissue. The device 10 can be cycled between the fully fired configuration and a partially armed configuration to acquire multiple tissue samples.

Vacuum Assisted and Spring-Loaded Core Biopsy Device Embodiment 2

FIG. 5 depicts another embodiment of a vacuum assisted and spring-loaded core biopsy device 60, which utilizes vacuum assistance to arm both the inner and outer cannulas and re-arm the inner cannula after firing. On the other hand, the device 10 depicted in FIG. 1 utilizes manual force to arm both the inner and outer cannulas and utilizes vacuum to re-arm the inner cannula after firing. As such, the device 60 depicted in FIG. 5 minimizes physician fatigue. The device 60 depicted in FIG. 5 also utilizes vacuum to assist the springs in firing the inner and outer cannulas. Consequently, the device 60 can generate greater firing force, and has greater control over the sequence of arming and firing of the inner and outer cannulas.

The device 60 includes a housing 62, an outer cannula 64 slidably disposed in the housing 62, and an inner cannula/cutter 68 coaxially and slidably disposed in the outer cannula 64. The outer cannula 64 has a sharpened distal end 65 and defines a side window 66 at the distal end thereof. The inner cannula 68 has an open distal end at least partially defined by a sharpened (e.g., annular) cutting surface. The device 60 also includes a pair of grips 70a, 70b configured to allow users to ergonomically manipulate the device 60. The device 60 further includes a first aspiration/vacuum port 72, a second aspiration/vacuum port 73, and an atmosphere a vent port 97.

Figure 6:
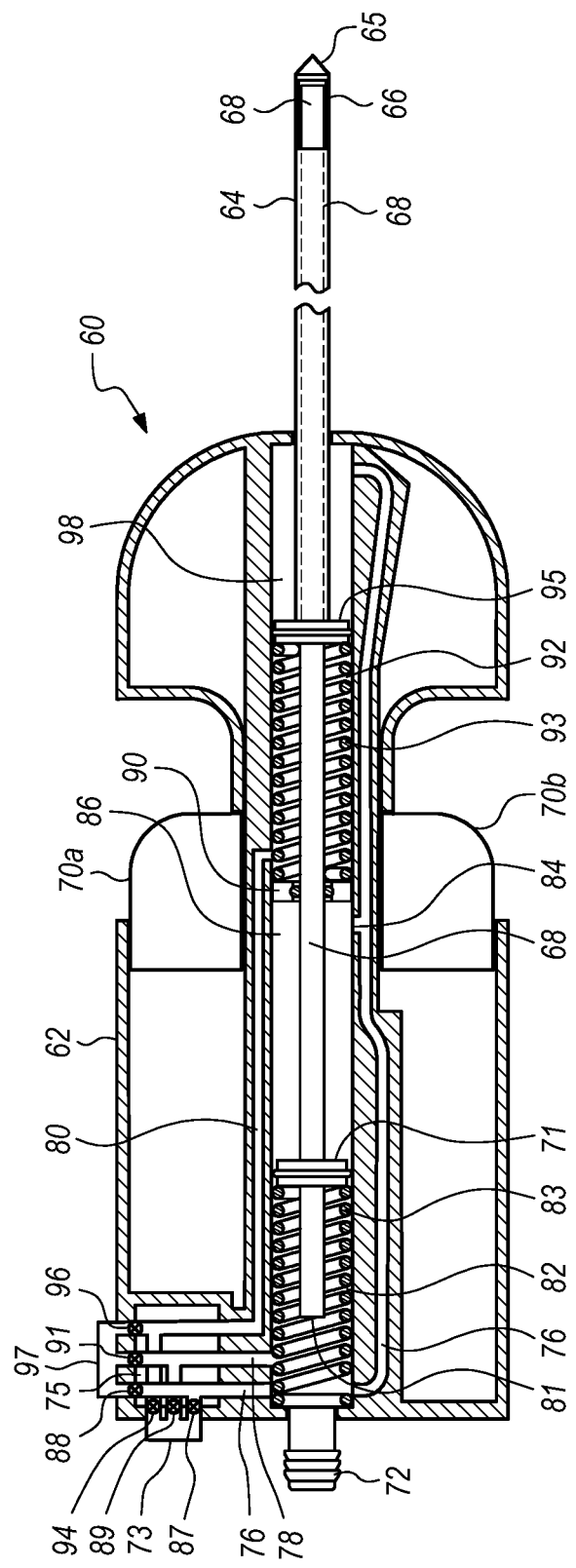
FIG. 6 is a side cross-sectional view of the biopsy device depicted in FIG. 5 in a fully armed configuration.

FIG. 6 depicts the vacuum assisted and spring-loaded core biopsy device 60 in a fully armed configuration. The inner cannula 68 is coupled to and passes through a proximal piston/seal 71. The proximal piston 71 and the housing 62 respectively define the distal and proximal ends of an inner cannula spring chamber 82 in which is disposed an inner cannula spring 83. While the inner cannula spring 83 is compressed in the fully armed configuration depicted in FIG. 6, the inner cannula spring 83 is biased to expand. The proximal piston 71 and wall 90 respectively define the proximal and distal ends of an inner cannula firing chamber 86.

The outer cannula 64 is coupled to a distal piston/seal 95. The distal piston 95 and wall 90 respectively define the distal and proximal ends of an outer cannula spring chamber 92 in which is disposed an outer cannula spring 93. While the outer cannula spring 93 is compressed in the fully armed configuration depicted in FIG. 6, the outer cannula spring 93 is biased to expand. The distal piston 95 and the housing 62 respectively define the proximal and distal ends of an outer cannula firing chamber 98.

The pneumatic system in the device 60 includes a valve assembly that allows the device 60 to utilize vacuum system assistance to arm both the inner and outer cannulas, re-arm the inner cannula after firing, and to assist the springs in firing the inner and outer cannulas. The pneumatic system also includes a first aspiration/vacuum port 72, a second aspiration/vacuum port 73, an atmosphere vent 97, and various lumens 76, 78, 80 all operatively coupled to the valve assembly 75. The first aspiration/vacuum port 72 is disposed adjacent an open proximal end 81 of the inner cannula 68 and functions to provide vacuum to draw tissue into the window 66 in the outer cannula 64 for biopsy sample collection. The second aspiration/vacuum port 73 and the atmosphere vent 97 are selectively coupled to the inner cannula spring chamber 82, the outer cannula spring chamber 92, the inner cannula firing chamber 86, and the outer cannula firing chamber 98 via various valves in the valve assembly 75 and various lumens 76, 78, 80. The first lumen 76 is fluidly coupled to the inner cannula firing chamber 86 and the inner cannula spring chamber 98. The second lumen 78 is fluidly coupled to the inner cannula spring chamber 82. The third lumen 80 is fluidly coupled to the outer cannula spring chamber 92.

The valve assembly 75 includes first, second, and third vacuum valves 87, 89, 94. The first vacuum valve 87 selectively fluidly couples the second aspiration/vacuum port 73 to the inner cannula firing chamber 86 and the outer cannula firing chamber 98 (via the first lumen 76) and a first atmosphere vent valve 88. The second vacuum valve 89 selectively fluidly couples the second aspiration/vacuum port 73 to the inner cannula spring chamber 82 (via the second lumen 78) and a second atmosphere vent valve 91. The third vacuum valve 94 selectively fluidly couples the second aspiration/vacuum port 73 to the outer cannula spring chamber 92 (via the third lumen 80) and a third atmosphere vent valve 96. The first second and third atmosphere vent valves 88, 91, 96 selectively fluidly couple the valve assembly 75 to the atmosphere vent port 97.

Movement of the proximal and distal seals 71, 95 and the inner and outer cannulas 68, 64 coupled thereto is controlled by pressure differentials in the inner cannula spring chamber 82/inner cannula firing chamber 86 and the outer cannula spring chamber 92/outer cannula firing chamber 98 respectively. The pressure differentials are in turn controlled by the many valves of the valve assembly 75.

In the fully armed configuration depicted in FIG. 6, the first vacuum valve 87 is closed and the first atmosphere vent valve 88 is open. This configuration of valves 87, 88 allows any vacuum in the inner cannula firing chamber 86 and the outer cannula firing chamber 98 to vent to atmosphere. At the same time, the second vacuum valve 89 is open and the second atmosphere vent valve 91 is closed. This configuration of valves 89, 91 allows vacuum from the second vacuum port 73 to be communicated to the inner cannula spring chamber 82. At the same time, the third vacuum valve 94 is open and the third atmosphere vent valve 96 is closed. This configuration of valves 94, 96 allows vacuum from the second vacuum port 73 to be communicated to the outer cannula spring chamber 92. The vacuum in the inner and outer cannula spring chambers 82, 92 and the venting in the inner cannula firing chamber 86 and the outer cannula firing chamber 98 moves the proximal and distal seals 71, 95 proximally, thereby compressing the inner and outer cannula springs 83, 93 and placing the device 60 in the fully armed configuration.

Figure 7:
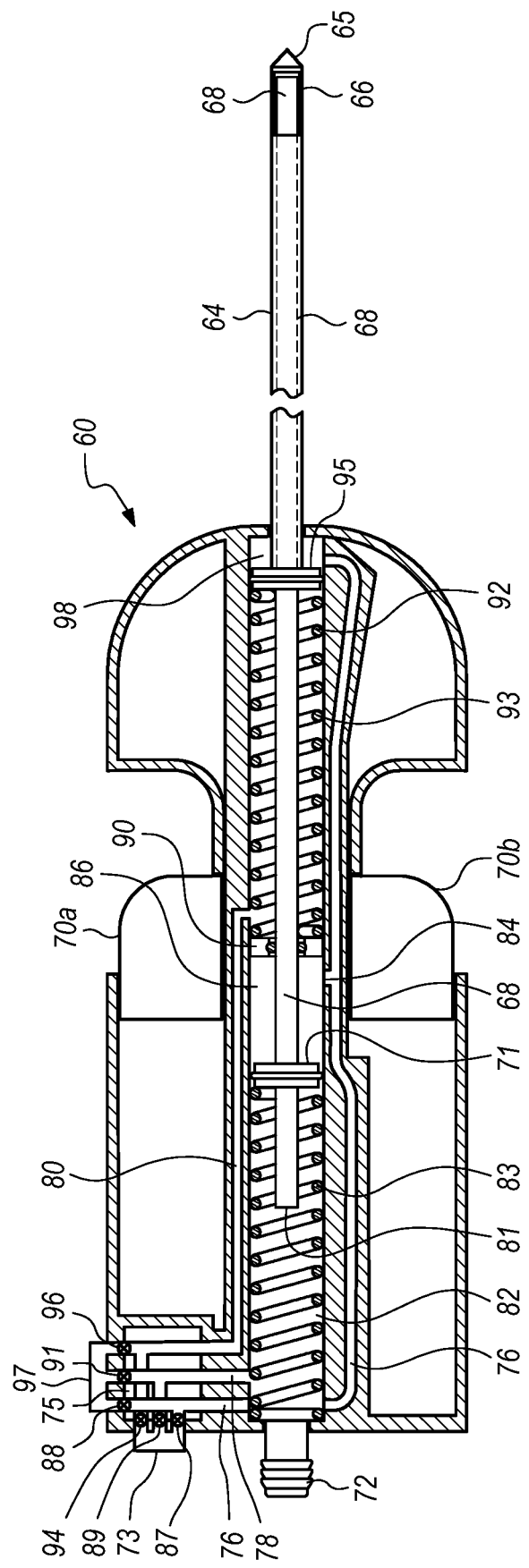
FIG. 7 is a side cross-sectional view of the biopsy device depicted in FIG. 5 in a fully fired configuration.

In the fully fired configuration depicted in FIG. 7, the first vacuum valve 87 is open and the first atmosphere vent valve 88 is closed. This configuration of valves 87, 88 allows vacuum from the second vacuum port 73 to be communicated to the inner cannula firing chamber 86 and the outer cannula firing chamber 98. At the same time, the second vacuum valve 89 is closed and the second atmosphere vent valve 91 is open. This configuration of valves 89, 91 allows any vacuum in the inner cannula spring chamber 82 to vent to atmosphere. At the same time, the third vacuum valve 94 is closed and the third atmosphere vent valve 96 is open. This configuration of valves 94, 96 allows any vacuum in the outer cannula spring chamber 92 to vent to atmosphere. The venting in the inner and outer cannula spring chambers 82, 92 allows the compressed inner and outer cannula springs 83, 93 to expand, moving the proximal and distal seals 71, 95 distally. The vacuum in the inner cannula firing chamber 86 and the outer cannula firing chamber 98 and the venting in the inner and outer cannula spring chambers 82, 92 also assists in moving the proximal and distal seals 71, 95 distally. This pneumatic arrangement and the expanding inner and outer cannula springs 83, 93 place the device 60 in the fully fired configuration.

Figure 8:
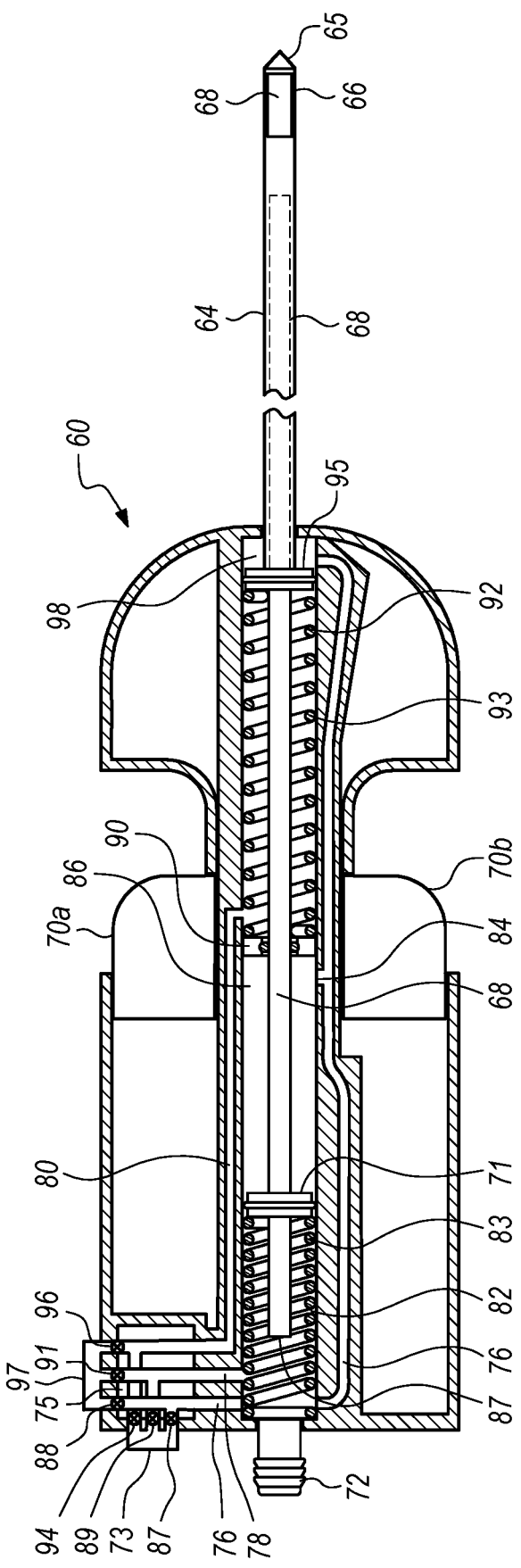
FIG. 8 is a side cross-sectional view of the biopsy device depicted in FIG. 5 in a partially armed configuration.

In the partially armed configuration depicted in FIG. 8, the first vacuum valve 87 is closed and the first atmosphere vent valve 88 is open. This configuration of valves 87, 88 allows any vacuum in the inner cannula firing chamber 86 and the outer cannula firing chamber 98 to vent to atmosphere. At the same time, the second vacuum valve 89 is open and the second atmosphere vent valve 91 is closed. This configuration of valves 89, 91 allows vacuum from the second vacuum port 73 to be communicated to the inner cannula spring chamber 82. At the same time, the third vacuum valve 94 is closed and the third atmosphere vent valve 96 is open. This configuration of valves 94, 96 allows any vacuum in the outer cannula spring chamber 92 to vent to atmosphere. The vacuum in the inner cannula spring chamber 82 and the venting in the inner cannula firing chamber 86 moves the proximal seal 71 proximally, thereby compressing the inner cannula spring 83 and placing the device 60 in the partially armed configuration.

With the device 60 in the partially armed configuration, the inner cannula 68 is withdrawn proximally relative to the outer cannula 64, which at least partially opens the side window 66 in the outer cannula 64. The vacuum exerted through the inner cannula 68 draws tissue through the side window 66 and into an interior of the outer cannula 64 for tissue sample collection. From the partially armed configuration, the valves 87, 88, 89, 91, 94, 96 in the valve assembly 75 can change to place the device 60 in the fully fired configuration to move the inner cannula 68 distally relative to the outer cannula 64 to separate the tissue drawn through the side window 66. Excising tissue pulled into the interior of the outer cannula 64 by the vacuum allows for clean tissue collection and minimizes damage to the surrounding tissue during sample collection.

As described above, before moving the device 60 from the fully fired configuration to the partially armed configuration, the user can manipulate the device 60 to move the window 66 in the patient's tissue. The device 60 can be cycled between the fully fired configuration and a partially armed configuration to acquire multiple tissue samples. Acquiring multiple tissue samples from an area in a patient can increase the diagnostic value of the biopsy samples. With the device 60 operating in a single insertion, multiple core mode, multiple tissue samples can be acquired while minimizing procedure time and patient discomfort.

The various valve changes can be triggered by a controller (not shown), such as an electronic or pneumatic controller. The controller may be operatively coupled to one or more actuators (e.g., the grips 70a, 70b).

Figure 9:
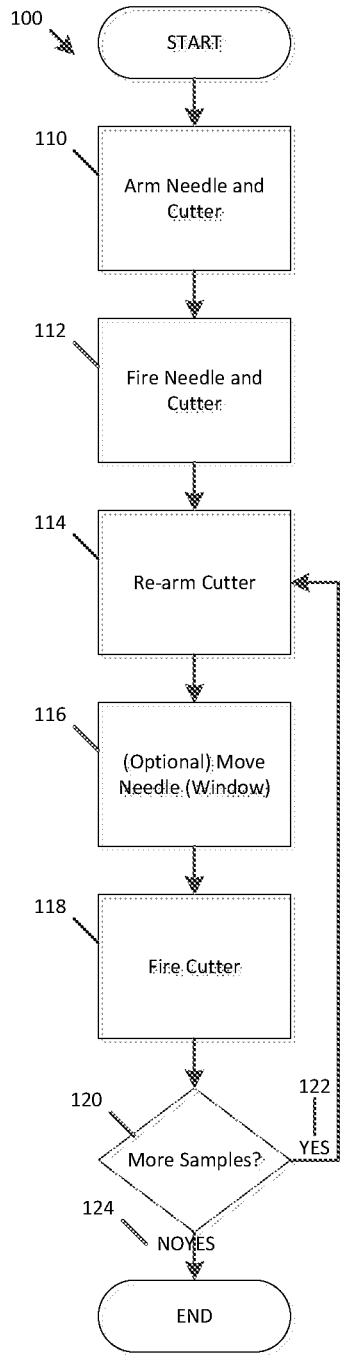
FIG. 9 is a flow chart illustrating a method for tissue biopsy according to some embodiments.

FIG. 9 depicts a method 100 for single insertion, multiple core tissue biopsy according to some embodiments. At step 110, the user arms a needle and a cutter of a biopsy device (e.g., devices 10 and 60 depicted in FIGS. 1-4B and 5-8, respectively). In device 10, the user can arm the needle and the cutter by moving sliders 20a, 20b proximally. In device 60, the user can arm the needle and the cutter by opening the second and third vacuum valves 89, 94 and the first atmosphere vent valve 88, and closing the second and third atmosphere vent valve 91, 96 and the first vacuum valve 87.

At step 112, the user fires the needle and the cutter into patient tissue. In device 10, the user can fire the needle and the cutter by depressing the actuator 26 to release the inner cannula proximal catch 54 from the housing catch 44. In device 60, the user can fire the needle and the cutter by opening the second and third atmosphere vent valves 91, 96 and the first vacuum valve 87, and closing the second and third vacuum valves 89, 94 and the first atmosphere vent valve 88.

At step 114, the user re-arms the cutter. In device 10, the user can re-arm the cutter by depressing the inner cannula arming valve 24. In device 60, the user can re-arm the cutter by opening the second vacuum valve 94 and the first atmosphere vent valve 88, and closing the second atmosphere vent valve 91 and the first vacuum valve 87.

At step 116, the user optionally moves the needle within the patient tissue. The user may rotate the needle and/or slide the needle along the needle track formed during insertion into the patient tissue.

At step 118, the user fires the re-armed cutter. In device 10, the user can fire the cutter by depressing the actuator 26 to release the inner cannula proximal catch 54 from the housing catch 44. In device 60, the user can fire the cutter by opening the second atmosphere vent valve 91 and the first vacuum valve 87, and closing the second vacuum valve 89 and the first atmosphere vent valve 88.

At step 120, the user decides whether additional samples are needed. If additional samples are needed 122, the method goes back to step 114. If no additional samples are needed 124, the method ends.

The method 100 described above allow users to perform single insertion, multiple core tissue biopsy using a vacuum to re-arm a previously fired cutter. Using a vacuum to compress the cutter firing spring minimizes procedure time, user fatigue, and unintended movement of the needle in the patient, which in turn minimizes user discomfort.

Other aspects of exemplary biopsy devices are described in U.S. patent application Ser. No. 14/555,531, filed Nov. 26, 2014; U.S. patent application Ser. No. 14/864,432, filed Sep. 24, 2014; U.S. patent application Ser. No. 14/497,046, filed Sep. 25, 2014; and U.S. patent application Ser. No. 15/024,631, filed Mar. 24, 2016. The above-referenced patent applications are assigned to the same assignee as the instant application, and the full contents thereof are hereby incorporated by reference as though fully set forth herein.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A handheld biopsy system, comprising:
a housing having a vacuum port;
an outer cannula movably coupled to the housing, the outer cannula comprising a lumen and a sharpened distal end;

an inner cannula slidably disposed in the lumen of the outer cannula, the inner cannula comprising an open distal end with a sharpened cutting surface and an open proximal end movably coupled to the housing, wherein the inner cannula is configured to repeatedly transition between a proximal, armed position, and a distal, fired position following insertion of the outer cannula into tissue, and to be re-armed, by transitioning from the fired position to the armed position, via a vacuum force from the vacuum port; and a specimen collection area in communication with the proximal open end of the inner cannula, wherein the biopsy system is configured to draw a sample into the open distal end of the inner cannula and into the specimen collection area via the vacuum force.

2. The handheld biopsy system of claim 1, further comprising:

a slider movably disposed in the housing, the slider defining an outer cannula spring chamber, wherein a proximal end portion of the outer cannula is coupled to the slider; and an outer cannula spring seated in the outer cannula spring chamber; wherein proximal movement of the slider relative to the housing compresses the outer cannula spring to arm the outer cannula.

3. The handheld biopsy system of claim 2, further comprising:

a spring compression member movably disposed in the housing, the spring compression member defining first and second inner cannula spring chambers, wherein a proximal portion of the inner cannula is coupled to the spring compression member; and a first inner cannula spring seated in the first inner cannula spring chamber and a second inner cannula spring seated in the second inner cannula spring chamber, wherein proximal movement of the spring compression member and the inner cannula relative to the housing compresses the first and second inner cannula springs to arm the inner cannula.

4. The handheld biopsy system of claim 3, further comprising:

a vacuum lumen in fluid communication with each of the vacuum port, the first inner cannula spring chamber and the second inner cannula spring chamber; and an inner cannula arming valve movably disposed in the vacuum lumen, the inner cannula arming valve being configured to selectively move between a closed position and an open position to re-arm the inner cannula.

5. The handheld biopsy system of claim 4, wherein:

when in the open position, the inner cannula arming valve is configured to simultaneously place the first and second inner cannula spring chambers in communication with the vacuum port to re-arm the inner cannula via the vacuum force; and when in the closed position, the inner cannula arming valve is configured to simultaneously isolate the first and second inner cannula spring chambers from the vacuum port.

6. The handheld biopsy system of claim 1, wherein the specimen collection area comprises one or more removeable cartridges in a proximal end of the biopsy system.

7. The handheld biopsy system of claim 6, wherein the one or more removeable cartridges are removably coupled to the open proximal end of the inner cannula.

8. The handheld biopsy system of claim 6, wherein the one or more removeable cartridges comprise a plurality of removeable cartridges.

9. The handheld biopsy system of claim 1, wherein the specimen collection area comprises one or more traps removably coupled between the vacuum port and a vacuum source.

10. A method for operating a biopsy device to collect multiple samples with a single insertion, the method comprising:

firing an inner cannula of a biopsy device to separate a first tissue sample from a patient, wherein the inner cannula is slidably disposed within a lumen of an outer cannula of the biopsy device, and wherein firing the inner cannula comprises transitioning the inner cannula from a proximal, armed position to a distal, fired position;

moving the separated first tissue sample through the inner cannula and into a collection area via a vacuum force;

without removing the outer cannula from the patient, re-arming the inner cannula via the vacuum force, wherein re-arming the inner cannula comprises moving the inner cannula from the fired position to the armed position;

firing the re-armed inner cannula to separate a second tissue sample from the patient; and moving the separated second tissue sample through the inner cannula and into the collection area via the vacuum force.

11. The method of claim 10, further comprising, prior to firing the inner cannula to separate the first tissue sample from the patient, firing the outer cannula to pierce a patient's skin, wherein firing the outer cannula comprises moving the outer cannula from a proximal, armed position to a distal, fired position.

12. The method of claim 10, wherein firing the inner cannula to separate the first tissue sample from the patient and firing the re-armed inner cannula to separate the second tissue sample from the patient respectively comprise cutting tissue extending through a window in a distal end of the outer cannula via a sharpened cutting surface at a distal end of the inner cannula.

13. The method of claim 10, further comprising:

after moving the separated second tissue sample into the collection area, without removing the outer cannula from the patient, re-arming the inner cannula via the vacuum force;

firing the re-armed inner cannula to separate a third tissue sample; and moving the separated third tissue sample through the inner cannula and into the collection area via the vacuum force.

14. The method of claim 10, wherein moving the separated first and second tissue samples through the inner cannula and into the collection area comprises moving the separated first and second tissue samples into one or more removeable cartridges in a proximal end of the biopsy device.

15. The method of claim 14, further comprising temporarily storing the first and second tissue samples in the one or removable cartridges.

16. The method of claim 15, further comprising removing the first and second tissue samples from the removable cartridges after tissue collection is complete.

17. The method of claim 10, wherein moving the separated first and second tissue samples through the inner cannula and into the collection area comprises moving the separated first and second tissue samples into one or more tissue traps disposed outside of the biopsy device.

18. The method of claim 17, further comprising temporarily storing the first and second tissue samples in the one or more tissue traps.

19. The method of claim 18, further comprising removing the first and second tissue samples from the tissue traps after tissue collection is complete.

20. The method of claim 10, further comprising, prior to firing the re-armed inner cannula, repositioning and/or rotating the outer cannula to a slightly different location within the patient, without removing the outer cannula from the patient.

\* \* \* \* \*